(12) United States Patent
Li et al.

(10) Patent No.: US 10,309,831 B2
(45) Date of Patent: Jun. 4, 2019

(54) DYNAMIC CALIBRATION METHOD FOR ECHELLE SPECTROMETER IN LASER-INDUCED BREAKDOWN SPECTROSCOPY

(71) Applicant: HUAZHONG UNIVERSITY OF SCIENCE AND TECHNOLOGY, Wuhan, Hubei (CN)

(72) Inventors: Xiangyou Li, Hubei (CN); Meng Shen, Hubei (CN); Zhongqi Hao, Hubei (CN); Xinyan Yang, Hubei (CN); Jiaming Li, Hubei (CN); Xiaoyan Zeng, Hubei (CN); Yongfeng Lu, Hubei (CN)

(73) Assignee: HUAZHONG UNIVERSITY OF SCIENCE AND TECHNOLOGY, Wuhan, Hubei (CN)

( * ) Notice: Subject to any disclaimer, the term of this patent is extended or adjusted under 35 U.S.C. 154(b) by 0 days.

(21) Appl. No.: 15/771,338

(22) PCT Filed: Apr. 24, 2017

(86) PCT No.: PCT/CN2017/081641
§ 371 (c)(1),
(2) Date: Apr. 26, 2018

(87) PCT Pub. No.: WO2018/184262
PCT Pub. Date: Oct. 11, 2018

(65) Prior Publication Data
US 2019/0003887 A1    Jan. 3, 2019

(30) Foreign Application Priority Data

Apr. 5, 2017   (CN) .......................... 2017 1 0217310 2

(51) Int. Cl.
| | |
|---|---|
| *G01J 3/02* | (2006.01) |
| *G01J 3/18* | (2006.01) |
| *G01J 3/443* | (2006.01) |
| *G01N 21/71* | (2006.01) |

(52) U.S. Cl.
CPC .......... *G01J 3/0297* (2013.01); *G01J 3/1809* (2013.01); *G01J 3/443* (2013.01); *G01N 21/718* (2013.01); *G01N 2201/127* (2013.01)

(58) Field of Classification Search
CPC ........ G01J 3/0297; G01J 3/1809; G01J 3/443; G01N 21/718; G01N 2201/127
USPC ......................................................... 356/318
See application file for complete search history.

(56) References Cited

U.S. PATENT DOCUMENTS

| | | | |
|---|---|---|---|
| 5,243,546 A | * | 9/1993 | Maggard ................... G01J 3/28 702/90 |
| 6,987,564 B2 | | 1/2006 | Gornushkin et al. |

(Continued)

FOREIGN PATENT DOCUMENTS

| | | |
|---|---|---|
| CN | 101750401 A | 6/2010 |
| CN | 102830096 A | 12/2012 |
| CN | 202661380 U | 1/2013 |
| CN | 103518121 A | 1/2014 |

OTHER PUBLICATIONS

International Search Report and Written Opinion issued in PCT/CN2017/081641, dated Dec. 29, 2017, 11 pages.

*Primary Examiner* — Hina F Ayub
(74) *Attorney, Agent, or Firm* — Hamre, Schumann, Mueller & Larson, P.C.

(57) ABSTRACT

The present invention belongs to the technical field of elemental analysis, and more particularly, relates to a dynamic calibration method for echelle spectrometer in laser-induced breakdown spectroscopy, comprising: S1: collecting a standard light source by using an echelle spectrometer; S2: in combination with a calibration function, calcu- (Continued)

ACCOMPANYING FIGURES lating a pixel position coordinate $(\hat{x},\hat{y})$ corresponding to a spectral wavelength $\hat{w}$; S3: performing dynamic searching and filtering near the pixel position coordinate $(\hat{x},\hat{y})$ to obtain a set D of all pixel position coordinates, and adjusting all original intensity values in the set D to obtain intensity values $F(I_{x,y})$, and S4: calculating a spectral line intensity value after dynamic calibration by summing the adjusted intensity values $F(I_{x,y})$, thereby completing dynamic calibration of the result of the echelle spectrometer. The method in the present invention can overcome the shortcoming, i.e., the existing echelle spectrometer is only calibrated before measurement without solving the spectral line drift during use, increasing the absolute intensity of the wavelength and reducing the detection limit of the quantitative analysis, as well as improving the precision of the quantitative analysis of an element to be analyzed.

5 Claims, 4 Drawing Sheets

(56) References Cited

U.S. PATENT DOCUMENTS

| | | | |
|---|---|---|---|
| 2005/0157293 A1* | 7/2005 | Florek | G01J 3/02 |
| | | | 356/328 |
| 2013/0112942 A1* | 5/2013 | Kurtin | C01B 19/007 |
| | | | 257/13 |
| 2016/0069745 A1 | 3/2016 | Wang et al. | |
| 2017/0268927 A1* | 9/2017 | Beardsley | G01J 3/0208 |

* cited by examiner

ACCOMPANYING FIGURES

DYNAMIC CALIBRATION METHOD FOR ECHELLE SPECTROMETER IN LASER-INDUCED BREAKDOWN SPECTROSCOPY

FIELD OF THE PRESENT INVENTION

The present invention belongs to the technical field of elemental analysis, and more particularly, relates to a dynamic calibration method for echelle spectrometer in laser-induced breakdown spectroscopy (LIES), which is capable of overcoming the shortcoming, i.e., the existing echelle spectrometer is only calibrated before measurement without solving the spectral line drift during use, so as to reduce the detection limit and improve the quantification precision in the LIES based analysis technology.

BACKGROUND OF THE PRESENT INVENTION

The LIES based analysis technology is a technology for determining material composition of the sample by analyzing the plasma spectra generated by laser bombardment of the sample. The laser-induced breakdown spectroscopy has a series of advantages such as fast analyzing speed, simple experimental conditions, remote and on-line analysis, and thus, is presenting a booming trend in many fields such as steel and special alloy detection, coal quality detection and environmental monitoring. Owing to the small size, wide spectral range, high resolution and other characteristics, the echelle spectrometer is widely used in this field. As a key component in the whole instrument, the reliability of the calibration method of the echelle spectrometer has a crucial influence on the sensitivity and precision of the LIBS detection technology.

In the existing calibration methods of the echelle spectrometer, calibration is performed before measurement with a standard calibration light source (e.g., a mercury lamp), and data obtained thereafter are all measured based on this calibration. However, due to the characteristic of the spatiotemporal instability of the laser-induced plasma, spectral drift often occurs during measurement, which then affects the spectral intensity and wavelength precision and ultimately affects the sensitivity and precision of the material composition analysis.

Due to the above defects, there is an urgent need to solve this problem, i.e., to design a calibration method for echelle spectrometer in LIBS so as to overcome the shortcoming, i.e., the existing echelle spectrometer is only calibrated before measurement without solving the spectral line drift during use.

SUMMARY OF THE PRESENT INVENTION

In view of the above-described defects or improvement requirement, the present invention provides a calibration method for echelle spectrometer in LIBS, in which dynamic searching is performed for the analytical spectrum lines of an element to be analyzed to select effective pixels, thereby overcoming the shortcoming, i.e., the existing echelle spectrometer is only calibrated before measurement without solving the spectral line drift during use. As a result, the absolute intensity of the analytical spectrum line is increased, and limit of detection of the quantitative analysis is reduced. Meanwhile, the improvement of the spectral wavelength accuracy also helps improve the precision of quantification.

In order to achieve the above objective, according to the present invention, there is provided a calibration method for echelle spectrometer in LIES, comprising:

S1: by using an echelle spectrometer, collecting a spectrogram of a standard calibration light source, and getting spectral wavelengths in different orders according to the spectrogram;

S2: based on information about the spectral wavelengths in different orders obtained in the step S1, and in combination with a corresponding calibration function $f(x,y)$, calculating a pixel position coordinate $(\hat{x},\hat{y})$ corresponding to a spectral wavelength $\hat{w}$ of a certain analysis element, where x and y respectively represent original pixel horizontal and vertical coordinates of an analysis element on the echelle spectrometer, and $\hat{x}$ and $\hat{y}$ respectively represent pixel horizontal and vertical coordinates corresponding to a spectral wavelength $\hat{w}$ of a certain analysis element on the echelle spectrometer;

S3: by using the echelle spectrometer, collecting laser-induced plasma spectra corresponding to the above analysis element in a sample to be tested, performing dynamic searching and filtering near the pixel position coordinate $(\hat{x},\hat{y})$ obtained in the step S2 to obtain a set D of all selected pixel position coordinates, and adjusting all original intensity values corresponding to the above analysis element in the set D to obtain adjusted intensity values expressed by an adjustment function $F(I_{x,y})$, where $I_{x,y}$ represents a spectral line intensity value at the pixel position coordinate (x,y), and x and y in the pixel position coordinate (x,y) in the set D respectively have lower limit values of m and n, and respectively have upper limit values of m' and n'; and S4: by using the adjusted intensity values $F(I_{x,y})$ obtained in the step S3, calculating a spectral intensity at the spectral wavelength $\hat{w}$, after dynamic calibration according to the following formula: $\hat{I}_{\hat{w}}=\Sigma_{x,y=m,n}^{m'n'}F(I_{x,y})$, which is used as the spectral intensity at the wavelength $\hat{w}$ of the analysis element, so that the dynamic calibration for the given spectral line of the echelle spectrometer is completed, where $I_{x,y}$ represents a spectral line intensity value at the pixel position coordinate (x,y) on the echelle spectrometer, the function F is an adjustment function, $\hat{I}_{\hat{w}}$ represents a spectral line intensity value corresponding to the spectral wavelength $\hat{w}$ after calibration and $\Sigma$ is a sum function.

Preferably, a selection range of the set D of pixel position coordinates in the step S3 is determined by the following steps: by taking a spectral intensity $\hat{q}$ as a judgment intensity, performing dynamic searching near the pixel position coordinate $(\hat{x},\hat{y})$, and if a synthetical intensity q at a certain pixel position coordinate is smaller than the judgment intensity $\hat{q}$, not adding the pixel position coordinate into the set D, otherwise, adding the pixel position coordinate into the set D. Many comparative experiments showed that after dynamic searching, useless pixels can be excluded to reduce the background intensity of the wavelength and then reduce the intensity fluctuation of the characteristic wavelength of the element, thereby effectively improving the analytical precision of quantitative calculation.

Further preferably, the calculation functions of the synthetical intensity q and the judgment intensity $\hat{q}$ are as follow:

$$q=[\exp(-z)-1]\cdot q_0$$

$$\hat{q}=q_0/2$$

$$z=k\cdot(x-\hat{x})^2+l\cdot(y-\hat{y})^2,$$

where z represents the distance between the pixel position coordinates (x,y) and ($\hat{x},\hat{y}$), $q_0$, represents the original intensity at the pixel position coordinate ($\hat{x},\hat{y}$), exp is an exponential function, and k and l represent weight coefficients which are determined by users in actual use.

Preferably, the dynamic searching near the pixel position coordinate ($\hat{x},\hat{y}$) in the step S3 is performed in a spiral movement manner. Many comparative experiments showed that by designing an appropriate synthetical intensity calculation function and selecting an appropriate judgment intensity, useless pixels can be excluded to reduce the background intensity of the wavelength and then reduce the intensity fluctuation of the characteristic wavelength of the element, thereby effectively improving the analytical precision of quantitative calculation.

Preferably, the adjustment function F in the step 3 is as follow:

$$F = I_{x,y} + |I_{x,y} - I_{\hat{x},\hat{y}}| \cdot [1 - \exp(-z)] \cdot v,$$

where z represents the distance between the pixel position coordinates (x,y) and ($\hat{x},\hat{y}$), $I_{\hat{x},\hat{y}}$ represents a spectral line intensity value at the pixel position coordinate ($\hat{x},\hat{y}$), $I_{x,y}$ represents a spectral line intensity value at the pixel position coordinate (x,y), exp is an exponential function, and v represents an adjustment coefficient which is determined by users in actual use.

Many comparative experiments showed that through the intensity adjustment function, the absolute intensity value of the spectrum can be optimized to reduce the intensity fluctuation of the wavelength, thereby effectively improving the analytical precision of quantitative calculation.

In general, compared with the prior art, the present invention has the following beneficial effects:

(1) in the method of the present invention, dynamic searching is performed on the spectrographs captured by the spectrometer of the analytical spectra of the element, which selects effective pixels, increases the absolute intensity of the wavelength, and thus effectively reduces the detection limit of the quantitative analysis. Meanwhile, increasing of the accuracy of the wavelength helps improve the precision of the quantitative analysis.

(2) in the method of the present invention, dynamic searching is performed on the spectrographs captured by the spectrometer detector of the analytical spectra of the element, which excludes useless pixels, reduces the background intensity of the wavelength, then reduces the intensity variation of the characteristic wavelength of the element and thus effectively improves the analytical precision of quantitative calculation.

(3) as a spectrum pretreatment method, the method of the present invention can be used in combination with various subsequent processing methods, such as univariate regression, multivariate regression, artificial neural network and support vector machine.

(4) as a software preprocessing method, the method of the present invention improves the analytical performance of the echelle spectrometer, and the method has simple steps, no equipment reforming cost, less calculation amount to be processed, rapid calculation process and high calculation precision, and thus has important application value.

DETAILED DESCRIPTION OF THE EMBODIMENTS

For clear understanding of the objectives, features and advantages of the present invention, detailed description of the present invention will be given below in conjunction with accompanying drawings and specific embodiments. It should be noted that the embodiments described herein are only meant to explain the present invention, and not to limit the range of the present invention.

Figure 1:
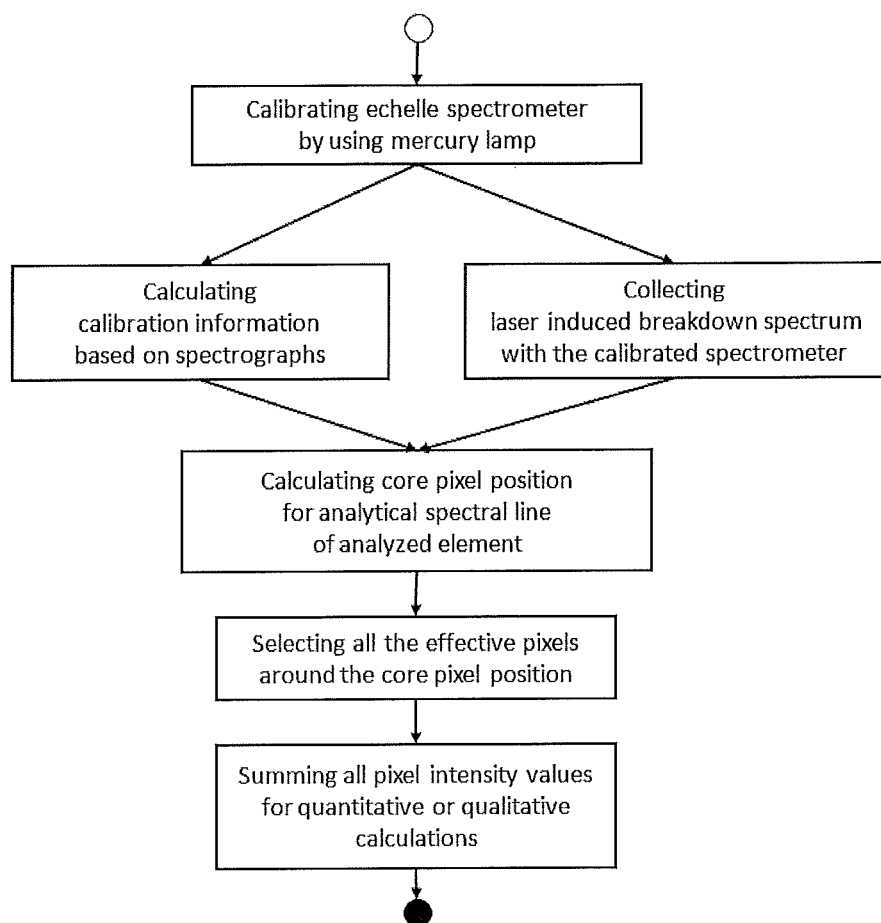
FIG. 1 is a flowchart of a dynamic calibration method for echelle spectrometer in LIBS according to the present invention.

FIG. 1 is a flowchart of a dynamic calibration method for echelle spectrometer in LIBS according to the present invention, and as shown in FIG. 1, the method specifically comprising the following steps:

S1: by using an echelle spectrometer, collecting a spectrogram of a standard calibration light source, and getting spectral wavelengths in different orders according to the spectrogram;

S2: based on information about the spectral wavelengths in different orders obtained in the step S1, and in combination with a corresponding calibration function $f(x,y)$, calculating a pixel position coordinate ($\hat{x},\hat{y}$) corresponding to a spectral wavelength $\hat{w}$ of a certain analysis element, where x and y respectively represent original pixel horizontal and vertical coordinates of an analysis element on the echelle spectrometer, and $\hat{x}$ and $\hat{y}$ respectively represent pixel horizontal and vertical coordinates corresponding to a spectral wavelength $\hat{w}$ of a certain analysis element on the echelle spectrometer;

S3: by using the echelle spectrometer, collecting laser-induced plasma spectra corresponding to the above analysis element in a sample to be tested, performing dynamic searching and filtering near the pixel position coordinate ($\hat{x},\hat{y}$) obtained in the step S2 to obtain a set D of all selected pixel position coordinates, and adjusting all original intensity values in the set D to obtain adjusted intensity values expressed by an adjustment function $F(I_{x,y})$, where $I_{x,y}$ represents a spectral line intensity value at the pixel position coordinate (x,y), and x and y in the pixel position coordinate (x,y) in the set D respectively have lower limit values of m and n, and respectively have upper limit values of m' and n'; and S4: by using the adjusted intensity values $F(I_{x,y})$ obtained in the step S3, calculating a spectral intensity at the spectral wavelength $\hat{w}$ after dynamic calibration according to the following formula: $\hat{I}_{\hat{w}} = \Sigma_{x,y=m,n}^{m'n'} F(I_{x,y})$, which is used as the spectral intensity at the wavelength $\hat{w}$ of the analysis element, so that the dynamic calibration for the given spectral line of the echelle spectrometer is completed, where $I_{x,y}$ represents a spectral line intensity value at the pixel position coordinate (x,y) on the echelle spectrometer, the function F is an adjustment function, $\hat{I}_{\hat{w}}$ represents a spectral line intensity value corresponding to the spectral wavelength $\hat{w}$ after calibration and $\Sigma$ is a sum function.

In a preferred embodiment of the present invention, a selection range of the set D of pixel position coordinates in the step S3 is determined by the following steps: by taking a spectral intensity $\hat{q}$ as a judgment intensity, performing dynamic searching near the pixel position coordinate $(\hat{x},\hat{y})$, and if a synthetical intensity q at a certain pixel position coordinate is smaller than the judgment intensity $\hat{q}$, not adding the pixel position coordinate into the set D, otherwise, adding the pixel position coordinate into the set D. Many comparative experiments showed that after dynamic searching, useless pixels can be excluded to reduce the background intensity of the wavelength and then reduce the intensity fluctuation of the characteristic wavelength of the element, thereby effectively improving the analytical precision of quantitative calculation.

In another preferred embodiment of the present invention, the calculation functions of the synthetical intensity q and the judgment intensity $\hat{q}$ are as follow:

$$q=[\exp(-z)-1]\cdot q_0$$

$$\hat{q}=q_0/2$$

$$z=k\cdot(x-\hat{x})^2+l\cdot(y-\hat{y})^2,$$

where z represents the distance between the pixel position coordinates (x,y) and $(\hat{x},\hat{y})$, $q_0$ represents the original intensity at the pixel position coordinate $(\hat{x},\hat{y})$, exp is an exponential function, and k and l represent weight coefficients which are determined by users in actual use.

In another preferred embodiment of the present invention, the dynamic searching near the pixel position coordinate $(\hat{x},\hat{y})$ in the step S3 is performed in a spiral movement manner. Many comparative experiments showed that by designing an appropriate synthetical intensity calculation function and selecting an appropriate judgment intensity, useless pixels can be excluded to reduce the background intensity of the wavelength and then reduce the intensity fluctuation of the characteristic wavelength of the element, thereby effectively improving the analytical precision of quantitative calculation.

In another preferred embodiment of the present invention, the adjustment function F in the step 3 is as follow:

$$F=I_{x,y}+|I_{x,y}-I_{\hat{x},\hat{y}}|\cdot[1-\exp(-z)]\cdot v,$$

where z represents the distance between the pixel position coordinates (x,y) and $(\hat{x},\hat{y})$, $I_{\hat{x},\hat{y}}$ represents a spectral line intensity value at the pixel position coordinate $(\hat{x},\hat{y})$, $I_{x,y}$ represents a spectral line intensity value at the pixel position coordinate (x,y), exp is an exponential function, and v represents an adjustment coefficient which is determined by users in actual use.

For better explanation of the present invention, a specific embodiment is given below.

Figure 2:
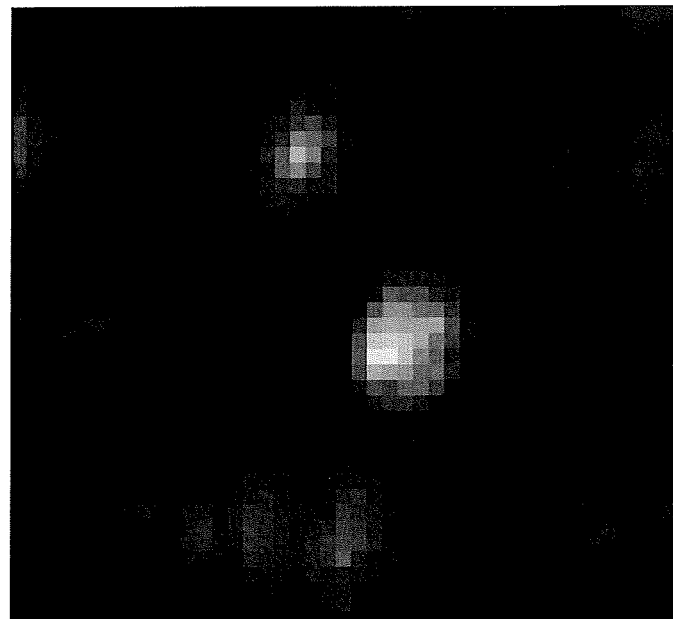
FIGS. 2(a) and 2(b) shows intensity drafting of LIBS on the detector of the echelle spectrometer.
Figure 2:
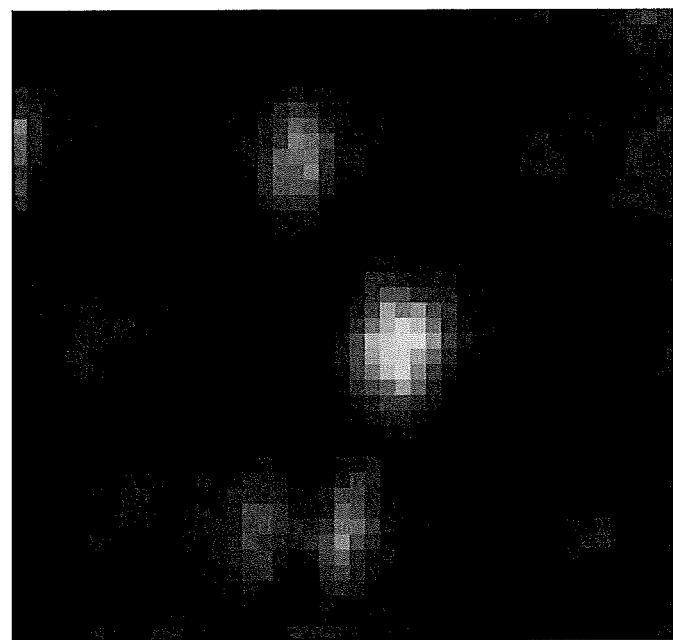
Figure 3:
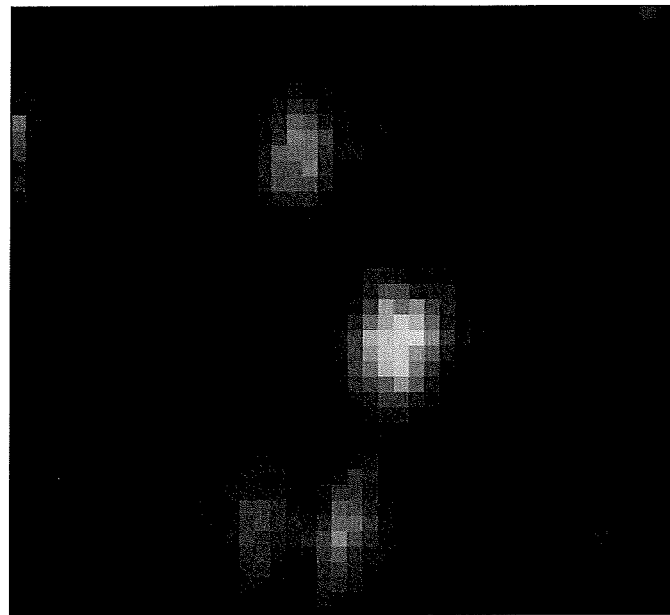
FIGS. 3(a) and 3(b) are comparison diagrams of results with and without an intensity adjustment function for LIBS according to the present invention.
Figure 3:
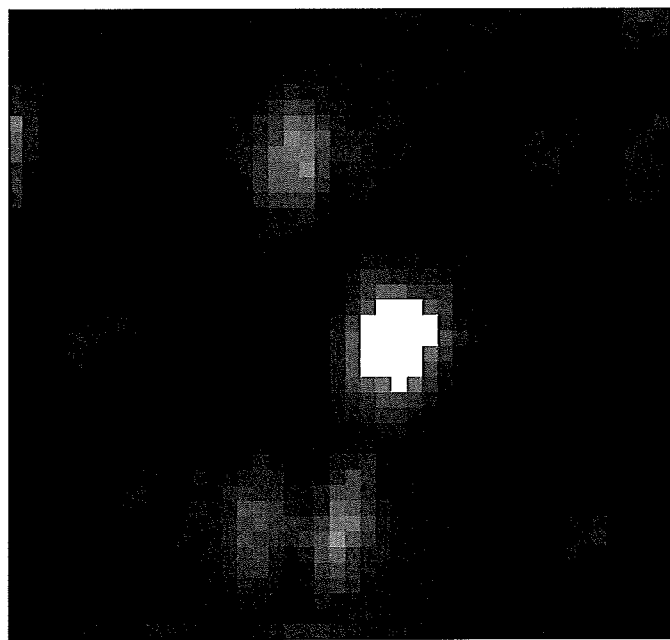

For the spectrographs of LIBS with an echelle spectrometer, the spectrographs tend to fluctuate within a small range due to the fluctuation characteristics of the plasma, as shown in FIG. 2. This fluctuating phenomenon is generated due to the spatiotemporal instability of the plasma generated by laser-matter interaction, and does not appear in other application fields of the echelle spectrometer. Therefore, this is also a prerequisite and a substantial problem to be solved in the method of the present invention.

In a first step, an echelle spectrometer is calibrated by a stabilized light source (a mercury lamp for spectrometer calibration), and linear fitting is performed on the calibrated spectral lines in all spectral orders to be processed so as to obtain a wavelength calibration function in a certain spectral order:

$$w=a\cdot x^2+b\cdot y^2+c\cdot x\cdot y+d\cdot x+e\cdot y+f,$$

where a, b, c, d, e and f are coefficients of the quadratic fitting curve, x and y are pixel position coordinate values on the echelle spectrometer detector. It should be noted here that the specific function used for wavelength calibration is not limited to the quadratic fitting function here, and any fitting function that converts a pixel position coordinate into a wavelength is included.

In a second step, for a certain wavelength (e.g., 403.2 nm) of an element (e.g., manganese) to be analyzed in a sample, its coordinate values on the detector are calculated. Since there may be multiple pixel position coordinates that satisfy the calculation result within a given error range, intensity values at the multiple pixel position coordinates are arranged and then a pixel position coordinate corresponding to the maximum intensity value is selected and denoted by $\hat{x}$ and $\hat{y}$.

It should be noted here that the determination of this pixel position coordinate is not limited to the use of the maximum intensity value of a single pixel as a criterion, and 2×2, 3×3 or multiple other combinations of pixel unit sizes may be selected. In addition, the intensity can also be calculated by weighted summation of the respective intensities of multiple pixel units. The essence of this step is to select the core imaging position of the plasma corresponding to this wavelength on the spectrometer detector, and any calculation process for this purpose can be used in this step.

In a third step, by taking the pixel position coordinate $\hat{x}$ and $\hat{y}$ as an initial position, a synthetical intensity q at the pixel position coordinate x and y near the pixel position coordinate $\hat{x}$ and $\hat{y}$ is calculated, and the calculation functions of the synthetical intensities q are as follow:

$$q=[\exp(-z)-1]\cdot q_0$$

$$z=k\cdot(x-\hat{x})^2+l\cdot(y-\hat{y})^2,$$

where z represents the distance between the pixel position coordinates (x,y) and $(\hat{x},\hat{y})$, $q_0$ represents the original intensity at the pixel position coordinate $(\hat{x},\hat{y})$, exp is an exponential function, and k and l represent weight coefficients which are determined by users in actual use.

The judgment intensity $\hat{q}$ can be calculated by the following formula:

$$\hat{q}=q_0/2$$

It should be noted here that the core of this step is to select all pixels in the appropriate range by taking the pixel position coordinate $\hat{x}$ and $\hat{y}$ obtained in the second step as the central point, and any calculation process for this purpose can be used in this step.

In a fourth step, the original intensity values at the pixel position coordinates obtained in the third step are adjusted, and the adjusted intensity values are summed to obtain a result value, which is used as the intensity value of the wavelength (403.2 nm) of the element (manganese) in the sample to be tested, and participates in subsequent quantitative or qualitative calculations.

The adjustment function F is as follow:

$$F=I_{x,y}+|I_{x,y}-I_{\hat{x},\hat{y}}|\cdot[1-\exp(-z)]\cdot v.$$

It should be noted here that that the core of this step is to dynamically adjust the original pixel intensity values selected in the third step, and any calculation process for this purpose can be used in this step.

Quantitative analysis of elements Mn, Cr and V in microalloyed steels is performed by the above method:

The experimental device is a standard laser-induced breakdown spectrometer. The experiment is carried out by an echelle spectrometer (Andor Technology, Mechelle5000) in an air atmosphere. A Nd:YAG pulsed laser (Brilliant B, wavelength: 532 nm) is used with a laser repetition frequency of 10 Hz and an average pulse energy of 70 mJ. Via a mirror and a convex lens, the laser is focused onto the surface of a sample which is placed on a three-dimensional platform for planar circular radiation motion. In the experiment, standard samples of microalloyed steel (No.: GSB03-2453-2008) are selected and the experiment is repeated 40 times for each sample.

Figure 4:
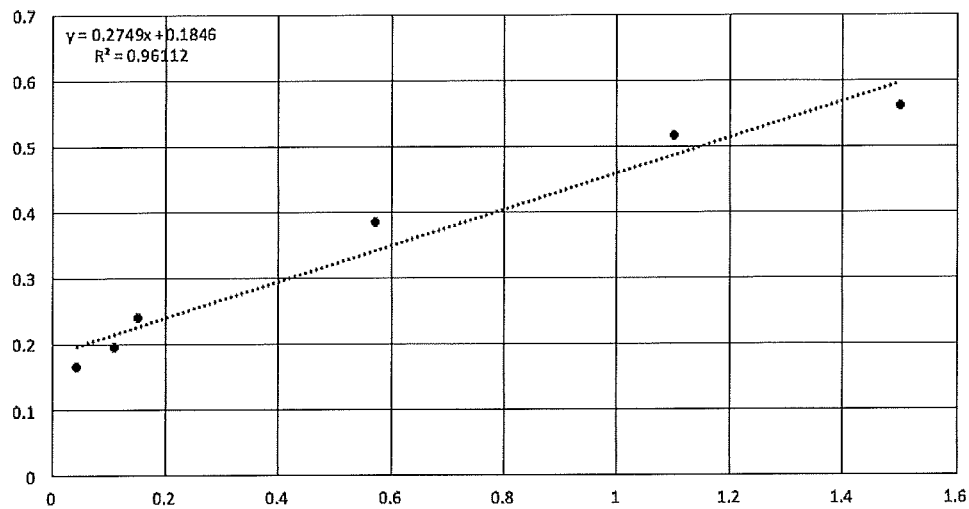
FIGS. 4(a) and 4(b) show fitted curves for manganese in a test sample adopting the conventional method and the method according to the present invention, respectively.
Figure 4:
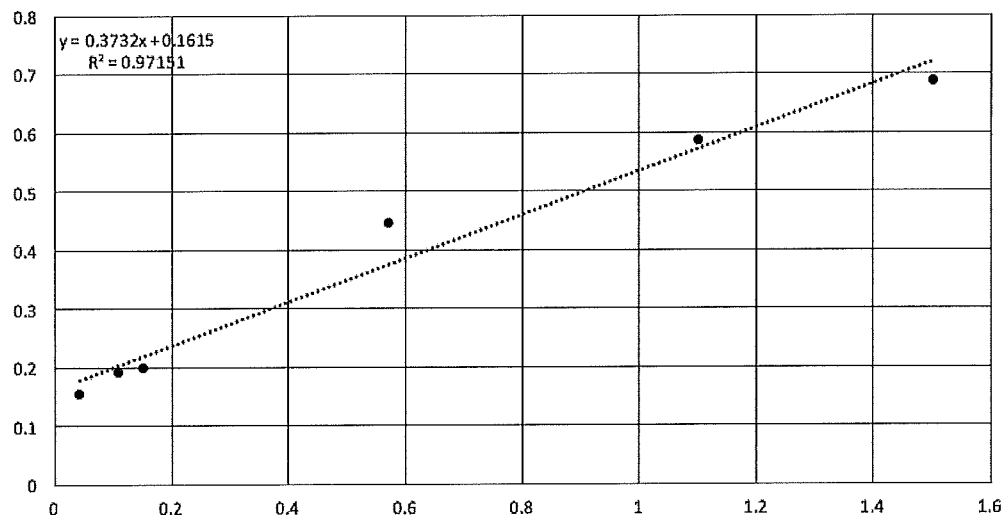

A wavelength of 403.2 nm is selected for the analysis element of Mn. In this case, this method reduces the detection limit by about 12.5% compared to the traditional quantitative analysis results, and the linear fitting correlation coefficient of the linear calibration curve is increased by about 1%. FIG. 4 show a comparison result of a fitted curve adopting the conventional method and a fitted curve adopting this method for the element Mn, in which FIG. 4(a) shows a fitted curve adopting the conventional method and FIG. 4(b) shows a fitted curve adopting this method.

A wavelength of 427.4 nm is selected for the analysis element of Cr. In this case, this method reduces the detection limit by about 10.2% compared to the traditional quantitative analysis results, and the linear fitting correlation coefficient of the linear calibration curve is increased by about 2%.

A wavelength of 440.8 nm is selected for the analysis element of V. In this case, this method reduces the detection limit by about 13.6% compared to the traditional quantitative analysis results, and the linear fitting correlation coefficient of the linear calibration curve is increased by about 5%.

While particular embodiments of the present invention have been shown and described, it will be obvious to those skilled in the art that changes and modifications may be made without departing from the spirit and range of the present invention.

The present invention claimed is:

1. A dynamic calibration method for echelle spectrometer in laser-induced breakdown spectroscopy, comprising:

S1: by using an echelle spectrometer, collecting a spectrogram of a standard calibration light source, and getting spectral wavelengths in different orders according to the spectrogram;

S2: based on information about the spectral wavelengths in different orders obtained in the step S1, and in combination with a corresponding calibration function $f(x,y)$, calculating a pixel position coordinate $(\hat{x},\hat{y})$ corresponding to a spectral wavelength $\hat{w}$ of a certain analysis element, where x and y respectively represent original pixel horizontal and vertical coordinates of an analysis element on the echelle spectrometer, and $\hat{x}$ and $\hat{y}$ respectively represent pixel horizontal and vertical coordinates corresponding to a spectral wavelength $\hat{w}$ of a certain analysis element on the echelle spectrometer;

S3: by using the echelle spectrometer, collecting laser-induced plasma spectra corresponding to the above analysis element in a sample to be tested, performing dynamic searching and filtering near the pixel position coordinate $(\hat{x},\hat{y})$ obtained in the step S2 to obtain a set D of all selected pixel position coordinates, and adjusting all original intensity values in the set D to obtain adjusted intensity values expressed by an adjustment function $F(I_{x,y})$, where $I_{x,y}$ represents a spectral line intensity value at the pixel position coordinate (x,y), and x and y in the pixel position coordinate (x,y) in the set D respectively have lower limit values of in and n, and respectively have upper limit values of m' and n'; and S4: by using the adjusted intensity values $F(I_{x,y})$ obtained in the step S3, calculating a spectral line intensity value at the spectral wavelength $\hat{w}$ after dynamic calibration according to the following formula: $\hat{I}_{\hat{w}}=\Sigma_{x,y=m,n}^{m'n'} F(I_{x,y})$, which is used as the spectral line intensity value at the wavelength $\hat{w}$ of the analysis element, so that the dynamic calibration for the given spectral line of the echelle spectrometer is completed, where $I_{x,y}$ represents a spectral line intensity value at the pixel position coordinate (x,y) on the echelle spectrometer, the function F is an adjustment function, $\hat{I}_{\hat{w}}$ represents a spectral line intensity value corresponding to the spectral wavelength $\hat{w}$ after calibration and $\Sigma$ is a sum function.

2. The dynamic calibration method of the echelle spectrometer of claim 1, wherein a selection range of the set D of pixel position coordinates in the step S3 is determined by the following steps: by taking a spectral intensity $\hat{q}$ as a judgment intensity, performing dynamic searching near the pixel position coordinate $(\hat{x},\hat{y})$, and if a synthetical intensity q at a certain pixel position coordinate is smaller than the judgment intensity $\hat{q}$, not adding the pixel position coordinate into the set D, otherwise, adding the pixel position coordinate into the set D.

3. The dynamic calibration method of the echelle spectrometer of claim 2, wherein the calculation functions of the synthetical intensity q and the judgment intensity $\hat{q}$ are as follow:

$q=[\exp(-z)-1]\cdot q_0$ $\hat{q}=q_0/2$ $z=k\cdot(x-\hat{x})^2+l\cdot(y-\hat{y})^2,$ where z represents the distance between the pixel position coordinates (x,y) and $(\hat{x},\hat{y})$, $q_0$ represents the original intensity at the pixel position coordinate $(\hat{x},\hat{y})$, exp is an exponential function, and k and l represent weight coefficients which are determined by users in actual use.

4. The dynamic calibration method of the echelle spectrometer of claim 3, wherein the dynamic searching near the pixel position coordinate $(\hat{x},\hat{y})$ in the step S3 is performed in a spiral movement manner.

5. The dynamic calibration method of the echelle spectrometer of claim 4, wherein the adjustment function F in the step 3 is as follow:

$F=I_{x,y}+|I_{x,y}-I_{\hat{x},\hat{y}}|\cdot[1-\exp(-z)]\cdot v,$ where z represents the distance between the pixel position coordinates (x,y) and $(\hat{x},\hat{y})$, $I_{\hat{x},\hat{y}}$ represents a spectral line intensity value at the pixel position coordinate $(\hat{x},\hat{y})$, $I_{x,y}$ represents a spectral line intensity value at the pixel position coordinate (x,y), exp is an exponential function, and v represents an adjustment coefficient which is determined by users in actual use.

* * * * *

UNITED STATES PATENT AND TRADEMARK OFFICE
CERTIFICATE OF CORRECTION

PATENT NO. : 10,309,831 B2
APPLICATION NO. : 15/771338
DATED : June 4, 2019
INVENTOR(S) : Li et al.

Page 1 of 1

It is certified that error appears in the above-identified patent and that said Letters Patent is hereby corrected as shown below:

On the Title Page

Item (72) the following inventor should be deleted:
"Yongfeing LU"

Signed and Sealed this
Fifth Day of May, 2020

Andrei Iancu
*Director of the United States Patent and Trademark Office*